United States Patent
Ogawa et al.

(10) Patent No.: US 11,234,648 B2
(45) Date of Patent: Feb. 1, 2022

(54) BIOLOGICAL MATERIAL MEASURING APPARATUS

(71) Applicant: Mitsubishi Electric Corporation, Chiyoda-ku (JP)

(72) Inventors: Shimpei Ogawa, Chiyoda-ku (JP); Daisuke Fujisawa, Chiyoda-ku (JP); Koichi Akiyama, Chiyoda-ku (JP); Kentaro Enoki, Chiyoda-ku (JP); Kosuke Shinohara, Chiyoda-ku (JP)

(73) Assignee: MITSUBISHI ELECTRIC CORPORATION, Tokyo (JP)

( * ) Notice: Subject to any disclaimer, the term of this patent is extended or adjusted under 35 U.S.C. 154(b) by 274 days.

(21) Appl. No.: 16/344,124

(22) PCT Filed: Aug. 25, 2017

(86) PCT No.: PCT/JP2017/030555
§ 371 (c)(1),
(2) Date: Apr. 23, 2019

(87) PCT Pub. No.: WO2018/123135
PCT Pub. Date: Jul. 5, 2018

(65) Prior Publication Data
US 2020/0060620 A1    Feb. 27, 2020

(30) Foreign Application Priority Data
Dec. 26, 2016 (JP) .............................. JP2016-251324

(51) Int. Cl.
*A61B 5/00* (2006.01)
*A61B 5/145* (2006.01)
*A61B 5/1455* (2006.01)

(52) U.S. Cl.
CPC .......... *A61B 5/6843* (2013.01); *A61B 5/0095* (2013.01); *A61B 5/1455* (2013.01); *A61B 5/14532* (2013.01); *A61B 2562/0261* (2013.01)

(58) Field of Classification Search
CPC .............. A61B 5/1455; A61B 5/14551; A61B 5/14532; A61B 5/14552; A61B 5/6843;
(Continued)

(56) References Cited

U.S. PATENT DOCUMENTS 6,128,091 A * 10/2000 Uchida ................ G01N 21/253
356/300
2004/0225206 A1* 11/2004 Kouchnir ........... A61B 5/14532
600/316
(Continued)

FOREIGN PATENT DOCUMENTS

CN 106102579 A 11/2016
JP 9-113439 A 5/1997
(Continued)

OTHER PUBLICATIONS

International Search Report dated Oct. 24, 2017 in PCT/JP2017/030555 filed on Aug. 25, 2017.
(Continued)

*Primary Examiner* — Chu Chuan Liu
(74) *Attorney, Agent, or Firm* — Xsensus LLP

(57) ABSTRACT

An infrared light source radiates infrared light. An ATR prism receives, on a first end face, the infrared light radiated from the infrared light source, causes the received infrared light to pass therethrough while repeating total reflection off a second end face and a third end face, and emits the infrared light that has passed therethrough from the third end face. An infrared photodetector detects the intensity of the infrared light emitted from the ATR prism. Strain sensors, which are contact sensors of one type, are attached to the ATR
(Continued)

prism and configured to detect a contact state between the ATR prism and a measurement skin.

14 Claims, 13 Drawing Sheets

(58) Field of Classification Search
CPC ..... A61B 5/0095; A61B 5/682; A61B 5/6813; A61B 5/0051
See application file for complete search history.

(56) References Cited

U.S. PATENT DOCUMENTS

| | | | |
|---|---|---|---|
| 2006/0119853 | A1 | 6/2006 | Baumberg et al. |
| 2006/0183982 | A1 | 8/2006 | Shioi |
| 2007/0282172 | A1 | 12/2007 | Toumazou et al. |
| 2011/0109907 | A1 | 5/2011 | Meyers et al. |
| 2015/0265190 | A1 | 9/2015 | Ikebe |
| 2015/0305621 | A1* | 10/2015 | Khan .................. A61B 5/6806 600/587 |
| 2017/0014321 | A1 | 5/2017 | Ikebe |

FOREIGN PATENT DOCUMENTS

| | | |
|---|---|---|
| JP | 2003-42952 A | 2/2003 |
| JP | 2005-73763 A | 3/2005 |
| JP | 2007-513669 A | 5/2007 |
| JP | 2008-519254 A | 6/2008 |
| JP | 2013-511041 A | 3/2013 |
| JP | 2015-121417 A | 7/2015 |
| JP | 2015-173935 A | 10/2015 |
| JP | 2015-198689 A | 11/2015 |
| WO | WO 2015/199159 A1 | 12/2015 |

OTHER PUBLICATIONS

Notice of Reasons for Refusal dated May 11, 2021 in Japanese Application No. 2020-106411.

Office Action dated Aug. 12, 2021, in corresponding German patent Application No. 112017006544.5, 23 pages.

Office Action dated Nov. 19, 2021, in corresponding Chinese patent Application No. 201780077002.2, 14 pages.

* cited by examiner

BIOLOGICAL MATERIAL MEASURING APPARATUS

TECHNICAL FIELD

The present invention relates to biological material measuring apparatuses, and more particularly, to a biological material measuring apparatus that uses infrared light to measure a biological material such as sugar in a living body.

BACKGROUND ART

A conventional invasive sensor draws blood with a needle and analyzes a component of a material in a living body. In particular, for blood sugar level sensors commonly used, a non-invasive type is desired to alleviate patient's pain caused by puncture. Although one type of non-invasive blood sugar level sensor using infrared light is capable of directly detecting a fingerprint spectrum of sugar, infrared light cannot reach a deep portion from a skin surface because infrared light is absorbed well by water. Under the circumstances, such a technique is demanded that detects a blood sugar level stably with high accuracy even when absorption by sugar in a living body is little.

In response to such a demand, for example, the apparatus described in PTL 1 (Japanese Patent Laying-Open No. 2003-42952) has an SN ratio improved through a measurement using an attenuated total reflection (ATR) prism. The infrared light propagating through the ATR prism repeats total reflection at an interface between a measurement skin and the ATR prism. Evanescent light is generated at the interface at which total reflection occurs, and then penetrates the measurement skin. Since the evanescent light is absorbed and scattered by water, sugar, and any other biological material, the intensity of the infrared light propagating through the ATR prism attenuates. Thus, the intensity of propagating infrared light attenuates more with a larger number of repetitions of total reflection. According to this literature, a semiconductor quantum cascade can be used as an infrared light source to miniaturize the infrared light source to be mounted in a mobile telephone.

PTL 2 (Japanese Patent Laying-Open No. 2015-173935) describes as follows. Considering that any gap between an ATR prism and a measurement skin can prevent infrared light from reaching the measurement skin, a force sensor is installed near the ATR prism in order to check a degree of adhesion between the ATR prism and the measurement skin.

CITATION LIST

Patent Literature

PTL 1: Japanese Patent Laying-Open No. 2003-42952
PTL 2: Japanese Patent Laying-Open No. 2015-173935

SUMMARY OF INVENTION

Technical Problem

A skin is composed of an epidermis near a skin surface and a corium below the epidermis. The epidermis includes a stratum corneum, a stratum granulosum, a stratum spinosum, and a stratum basale in order from the vicinity of the skin surface. Sugar and any other biological material, which are present in an interstitial fluid of the epidermis, are conceivably distributed nonuniformly in the depth direction while reflecting the structure of the epidermis.

When the epidermis receives a stress due to a contact between the ATR prism and the skin surface, the structure of the epidermis becomes distorted. Since a change in the contact state between the ATR prism and the skin surface changes the contact stress which the skin surface receives from the ATR prism, the distribution of the interstitial fluid in the epidermis also changes. This may lead to variations in the intensity of the evanescent light of infrared light which is absorbed by sugar and any other biological material.

According to PTL 2, though the force sensor installed near the ATR prism indirectly monitors the presence or absence of a gap, the contact state between the ATR prism and the measurement skin is not necessarily measured with high accuracy.

The present invention therefore has an object to provide a biological material measuring apparatus that can measure a contact state between an ATR prism and a measurement skin with high accuracy and then measure an amount of a biological material in the measurement skin.

Solution to Problem

A biological material measuring apparatus according to an aspect of the present invention includes an infrared light source, an ATR prism, an infrared photodetector, and a contact sensor. The infrared light source is configured to radiate infrared light in entirety or part of a wavelength range with absorption wavelengths of a biological material. The ATR prism is configured to receive, on a first end face, infrared light radiated from the infrared light source, cause the received infrared light to pass therethrough while repeating total reflection off a second end face and a third end face, and emit the infrared light that has passed therethrough from a fourth end face. The infrared photodetector is configured to detect the infrared light emitted from the ATR prism while separating wavelengths. The contact sensor is attached to the ATR prism and configured to detect a contact state between the ATR prism and a living body surface.

Advantageous Effects of Invention

According to the aspect of the present invention, the use of the contact sensor enables high-accuracy measurement of a contact state between an ATR prism and a measurement skin.

DESCRIPTION OF EMBODIMENTS

Embodiments of the present invention will now be described with reference to the drawings.

Embodiment 1

Although description will be given below by taking a blood sugar level as an example of a measuring object, a measuring apparatus of the present invention is applicable to measurement of a blood sugar level, as well as measurement of any other biological material.

Figure 1:
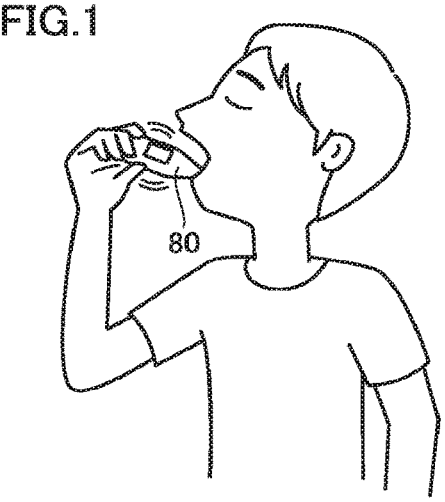
FIG. 1 shows an example use of a mobile non-invasive blood sugar level sensor 80 of an embodiment.

FIG. 1 shows an example use of a mobile non-invasive blood sugar level sensor 80 according to an embodiment.

As shown in FIG. 1, the blood sugar level of a living body of a subject is measured while bringing the head of mobile non-invasive blood sugar level sensor 80 into contact with a subject's lip with a thin keratin layer. Although a measurement site is desirably a lip with a thin keratin layer, it may be another site. It suffices that the measurement site is other than a site with a thick keratin layer, such as a palm. For example, measurements can also be made on a cheek of a face, an earlobe, and the back of a hand.

Figure 2:
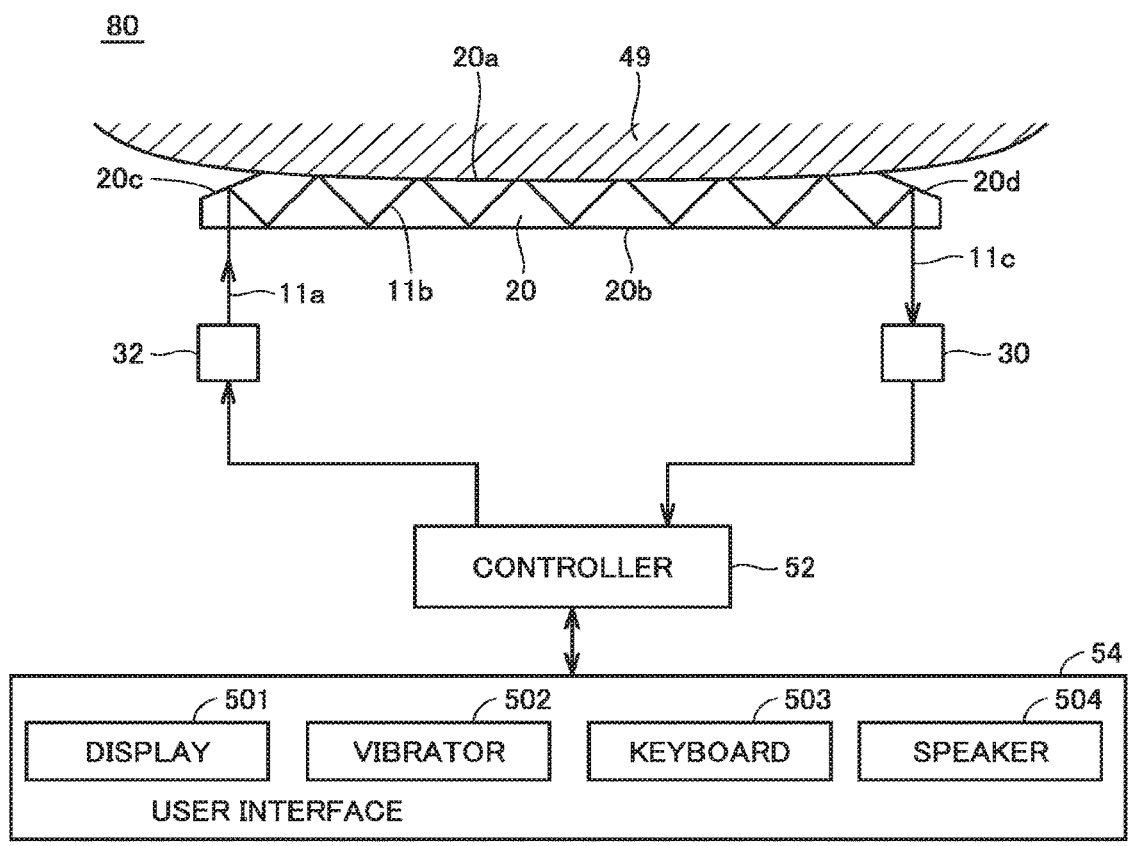
FIG. 2 shows a configuration of mobile non-invasive blood sugar level sensor 80 of Embodiment 1.

FIG. 2 shows a configuration of mobile non-invasive blood sugar level sensor 80 of Embodiment 1.

Non-invasive blood sugar level sensor 80 includes an ATR prism 20, an infrared light source 32, an infrared photodetector 30, a controller 52, and a user interface 54.

Infrared light source 32 radiates infrared light in entirety or part of a wavelength region with absorption wavelengths of a biological material.

Infrared photodetector 30 detects infrared light emitted from ATR prism 20.

Controller 52 controls infrared light source 32 and infrared photodetector 30. Controller 52 calculates the concentration of the blood sugar level of a living body based on the intensity of the infrared light detected by infrared photodetector 30.

User interface 54 includes a display 501, a vibrator 502, and a keyboard 503.

Figure 3:
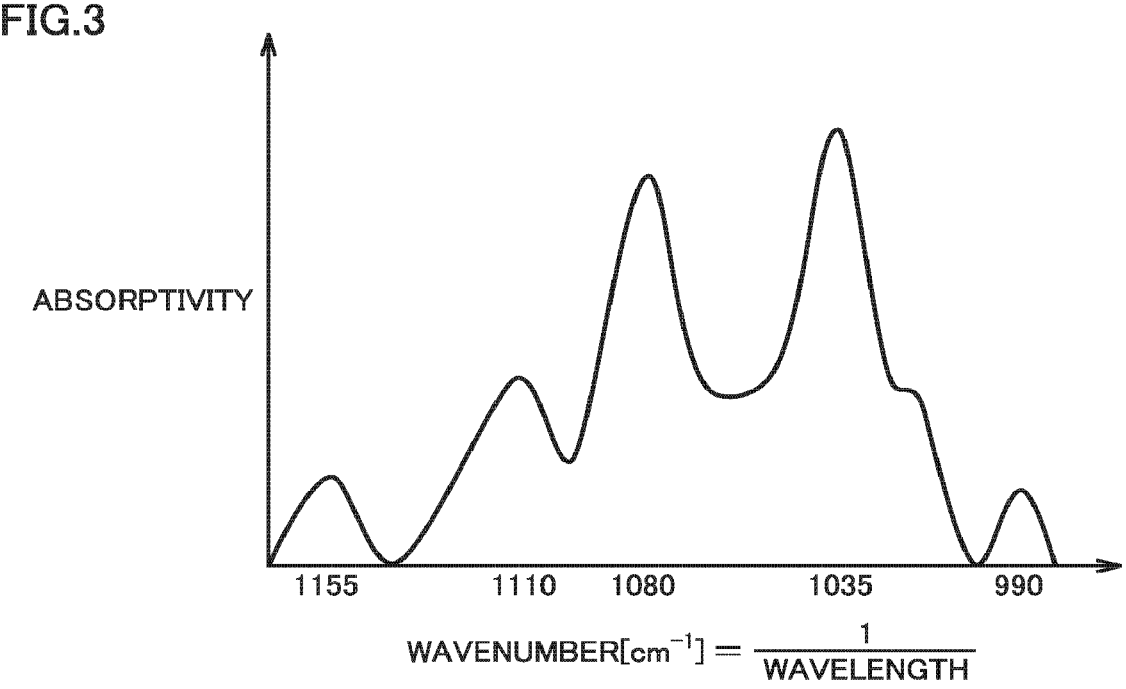
FIG. 3 shows a fingerprint spectrum of sugar.

ATR prism 20 is mounted on the head of non-invasive blood sugar level sensor 80. ATR prism 20 is in contact with a measurement skin 49, which is the surface of a living body of a subject. As shown in FIG. 1, when non-invasive blood sugar level sensor 80 is activated with ATR prism 20 brought into contact with a living body surface of the subject, infrared light source 32 radiates infrared light in entirety or part of the wavelength region in the wavelength range of 8.5 µm to 10 µm, which includes a fingerprint spectrum of sugar. FIG. 3 shows a fingerprint spectrum of sugar.

Incoming infrared light 11a emitted from infrared light source 32 is reflected off an end face 20c of ATR prism 20 and then turns into propagating infrared light 11b. Propagating infrared light 11b passes through ATR prism 20 being in contact with measurement skin 49 while repeating total reflection off end faces 20a and 20b of ATR prism 20. Propagating infrared light 11b that has passed through ATR prism 20 is reflected off an end face 20d of ATR prism 20 and then turns into radiated infrared light 11c. Infrared photodetector 30 detects the intensity of radiated infrared light 11c.

Evanescent light is generated at the interface (end face 20a) between ATR prism 20 and measurement skin 49 in total reflection. This evanescent light penetrates measurement skin 49 and is absorbed by sugar.

A smaller difference in the refractive index between the skin and ATR prism 20 results in more intense evanescent light. The evanescent light which has leaked from ATR prism 20 toward measurement skin 49 in total reflection at the interface (end face 20a) is absorbed by the biological material in measurement skin 49, so that the intensity of the infrared light subjected to total reflection at end face 20a attenuates. A larger amount of biological material in measurement skin 49 accordingly leads to more absorption of evanescent light, resulting in more attenuation of the intensity of the infrared light subjected to total reflection.

A skin is composed of an epidermis near a skin surface and a corium below the epidermis. The epidermis includes a stratum corneum, a stratum granulosum, a stratum spinosum, and a stratum basale in order from the vicinity of the skin surface, the thicknesses of which are about 10 µm, about several micrometers, about 100 µm, and about several micrometers, respectively. Cells are produced in the stratum basale and stacked on the stratum spinosum. Since water (interstitial fluid) does not reach the stratum granulosum, the cells die out. The dead cells are hardened in the stratum corneum. Sugar and any other biological material are present in the interstitial fluid of the epidermis. The interstitial fluid increases from the stratum corneum to the stratum spinosum. The intensity of the infrared light subjected to total reflection accordingly changes in accordance with a length by which evanescent light penetrates the stratum corneum.

Evanescent light attenuates exponentially from the interface toward measurement skin 49, and has a penetration length approximately equal to its wavelength. Spectroscopy using ATR prism 20 can thus measure an amount of a biological material in the region up to the penetration length. For example, a fingerprint spectrum of sugar has wavelengths of 8.5 µm to 10 µm, and accordingly, an amount of sugar in the region of about 8.5 µm to 10 µm from the prism surface of ATR prism 20 can be detected.

Figure 4:
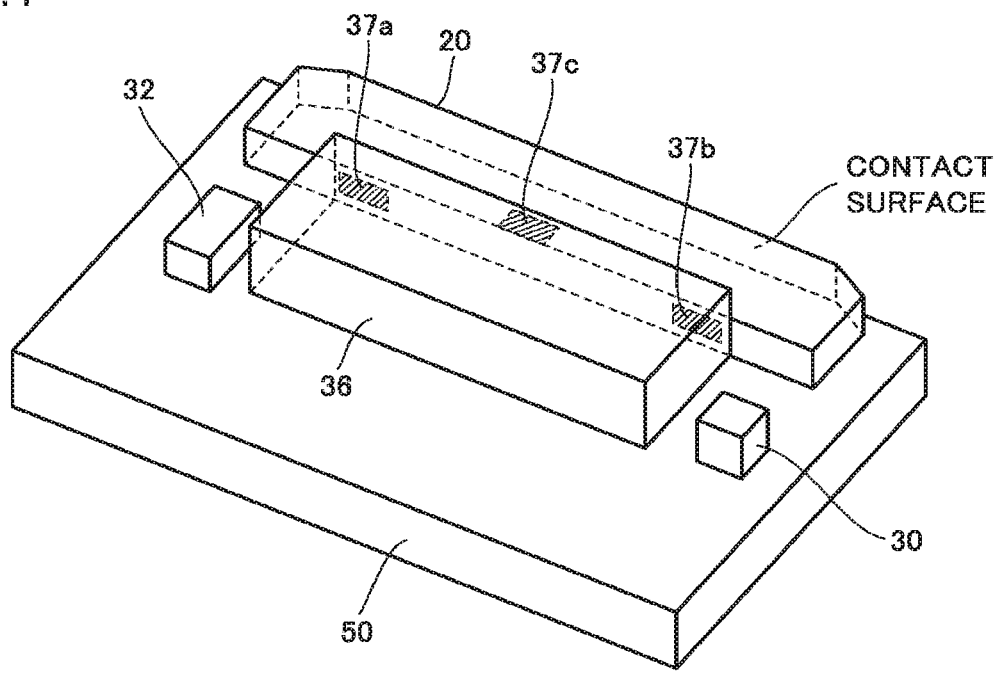
FIG. 4 shows the structure of a head of non-invasive blood sugar level sensor 80 of Embodiment 1.

FIG. 4 shows the structure of the head of non-invasive blood sugar level sensor 80 of Embodiment 1. This head includes a substrate 50, ATR prism 20, infrared light source 32, infrared photodetector 30, a support 36, and strain sensors 37a, 37b, and 37c.

ATR prism 20 has a shape of a rectangular parallelepiped with missing parts. The cross-section of the ATR prism has a shape obtained by cutting two vertical angles from a rectangle at a certain angle. A shorter surface on which vertical angles are cut as shown in FIG. 4 is brought into contact with the skin as a measuring surface that is in contact with measurement skin 49. The angle of end face 20c of ATR prism 20 is set such that propagating infrared light 11b in ATR prism 20 undergoes total reflection off end faces 20a and 20b of ATR prism 20. The angle of end face 20d of ATR prism 20 is set such that radiated infrared light 11c travels toward infrared photodetector 30.

Antireflection coating is applied to end face 20c on which incoming infrared light 11a from infrared light source 32 is incident and end face 20d from which radiated infrared light 11c exits toward infrared photodetector 30. Alternatively, incoming infrared light 11a from infrared light source 32 may be made p-polarized light (polarization is parallel to substrate 50), and incidence surface 20c and emission surface 20d may be chipped to make an angle of incidence/emission a Brewster's angle.

Used as the material for ATR prism 20 is a single crystal of zinc sulfide (ZnS) which is transparent in a mid-infrared range and has a relatively low refractive index. The material for ATR prism 20 is not limited to a single crystal of zinc sulfide (ZnS) and may be a known material such as zinc selenide (ZnSe). Contact surface 20a of ATR prism 20 which comes into contact with the skin is coated with a thin film of, for example, $SiO_2$ or SiN to cause no harm to a human body.

Used as infrared light source 32 is, for example, a quantum cascade laser module. A quantum cascade laser, which includes a single light source and has a high output and a high signal-to-noise ratio (SN ratio), is capable of high-accuracy measurements. A lens for collimating a beam is mounted in the quantum cascade laser module. The quantum cascade laser radiates infrared light in entirety or part of the wavelength region in the wavelength range of 8.5 µm to 10 µm.

Infrared light source 32 radiates infrared light in entirety or part of the wavelength region in the wavelength range of 8.5 µm to 10 µm, which includes the wavelengths of a fingerprint spectrum of sugar.

Infrared photodetector 30 is a sensor module with a micro electro mechanical system (MEMS) sensor or a non-cooling sensor such as a thermopile mounted therein. The sensor module includes an electric circuit such as a preamplifier and a lens for collecting light on a sensor device.

Figure 5:
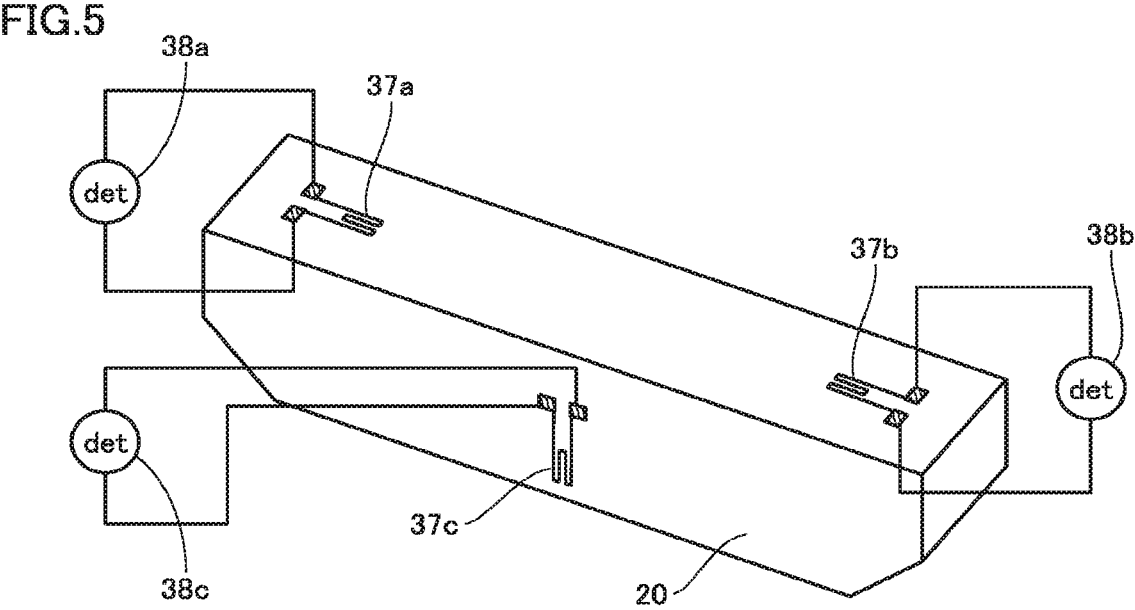
FIG. 5 is a diagram for illustrating a method of measuring a contact state between a measurement skin 49 and an ATR prism 20 using strain sensors 37*a*, 37*b*, and 37*c*.

FIG. 5 is a diagram for illustrating a method of measuring a contact state between measurement skin 49 and ATR prism 20 using strain sensors 37a, 37b, and 37c.

As shown in FIG. 4, ATR prism 20, infrared light source 32, infrared photodetector 30, and support 36 are disposed on substrate 50.

Support 36 supports ATR prism 20.

Strain sensors 37a, 37b, and 37c that are contact sensors of one type for measuring a stress from the contact surface between measurement skin 49 and ATR prism 20 is attached to ATR prism 20. Strain sensors 37a, 37b, and 37c measure the stress between substrate 50 and support 36. Strain sensors 37a, 37b, and 37c are positioned so as not to be in direct contact with measurement skin 49.

A first surface of a plurality of surfaces of ATR prism 20, which is perpendicular to a measuring surface that is in contact with measurement skin 49, is in contact with substrate 50.

A second surface of the plurality of surfaces of ATR prism 20, which is opposite to the measuring surface that is in contact with measurement skin 49, is in contact with support 36.

Strain sensors 37a and 37b are attached to the second surface, that is, the surface of ATR prism 20 which is in contact with support 36. Strain sensor 37c is attached to the first surface, that is, the surface of ATR prism 20 which is in contact with substrate 50.

Measurement circuits 38a, 38b, and 38c measure the resistance values of strain sensors 37a, 37b, and 37c, respectively.

Strain sensors 37a and 37b are provided on the contact surface between support 36 and ATR prism 20, which allows acquisition of information not only on the contact stress between ATR prism 20 and measurement skin 49 but also on the contact angle therebetween. For example, a press force can be calculated from an average of the output values of strain sensors 37a and 37b. A longitudinal contact angle of ATR prism 20 can be calculated from a difference value between the output values of strain sensors 37a and 37b. Information on a transverse contact angle can be obtained using the average of the output values of strain sensor 37a and strain sensor 37b, as well as the output value from strain sensor 37c.

Strain sensors 37a, 37b, and 37c may be thin metal lines having a resistance changing due to expansion and contraction strains which are caused by an exerted force. Assume that upon application of strains to the metal thin line, a resistance R changes by ΔR when a length L changes by ΔL, an expression below holds:

$$(\Delta R/R) = K_s \cdot (\Delta L/L) = k_s \cdot \varepsilon \quad (1)$$

where Ks is a coefficient representing the sensitivity of a strain gauge, and E is an amount of strain. Since ΔR is small, a Wheatstone bridge circuit is used.

Controller 52 determines lengths ΔLa, ΔLb, and ΔLc which have changed from the initial values (the lengths when ATR prism 20 is not in contact with measurement skin 4) of strain sensors 37a, 37b, and 37c using resistances Ra, Rb, and Rc of strain sensors 37a, 37b, and 37c which are supplied from measurement circuits 38a, 38b, and 38c and initial values Ra0, Rb0, and Rc0 (the resistance values when ATR prism 20 is not in contact with measurement skin 49) of resistances Ra, Rb, and Rc. Controller 52 calculates a contact stress and a contact angle between ATR prism 20 and measurement skin 49 based on ΔLa, ΔLb, and ΔLc, as described above.

In the present embodiment as described above, strain sensors 37a, 37b, and 37c calculate the contact stress between ATR prism 20 and measurement skin 49, enabling measurements without direct contact between strain sensors 37a, 37b, and 37c and measurement skin 49. The present embodiment can accordingly reduce the subject's burden in measurement because the degree of freedom of the contact region between ATR prism 20 and measurement skin 49 increases. The present embodiment also increases accuracy in measurement because a measurement region becomes larger.

Figure 6:
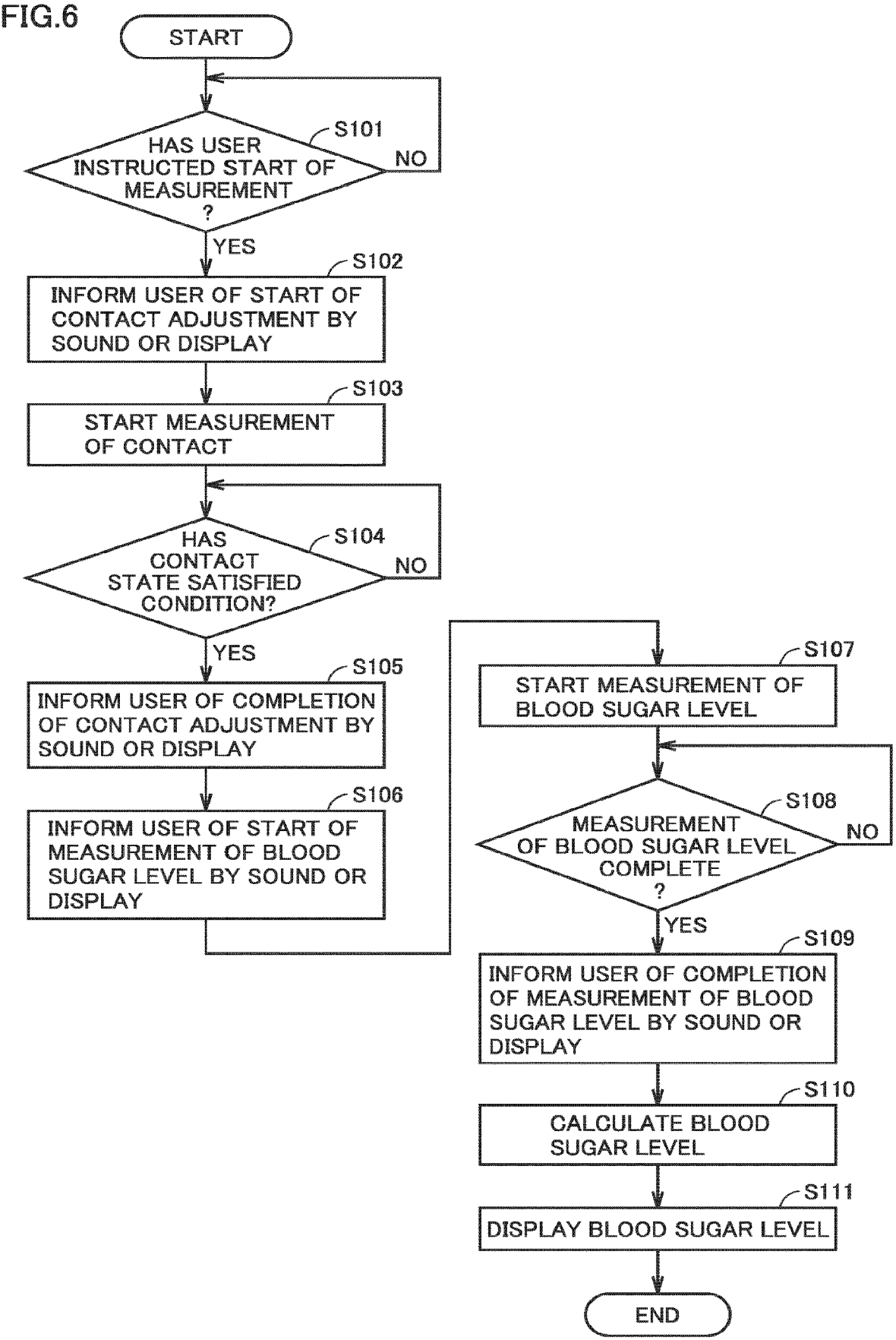
FIG. 6 is a flowchart showing an operational procedure of the non-invasive blood sugar level sensor of Embodiment 1.

FIG. 6 is a flowchart showing an operational procedure of the non-invasive blood sugar level sensor of Embodiment 1.

At step S101, controller 52 determines whether a start of measurement has been instructed through keyboard 503. If the user has instructed a start of measurement, the process proceeds to step S102.

At step S102, controller 52 causes speaker 504 to output a message voice or causes vibrator 502 to vibrate, thereby conveying a message for urging the user to start contact of ATR prism 20 with sensor array measurement skin 49. For example, a message voice "To prepare for measurement, bring sensor tip into contact with lip" is output. A massage voice, for example, "Adjust sensor tip" may be further output to urge the user to adjust the contact portion.

At step S103, controller 52 starts measuring the contact state between ATR prism 20 and measurement skin 49. Controller 52 calculates the contact state, that is, a contact stress and a contact angle, between ATR prism 20 and measurement skin 49 based on the resistance values of strain sensors 37a, 37b, and 37c.

At step S104, controller 52 determines whether the measured contact state has satisfied a condition for securing measurement accuracy. The condition herein is, for example, whether the contact stress falls within a predetermined range or is greater than or equal to a certain threshold. If the condition has been satisfied, the process proceeds to step S105.

At step S105, controller 52 outputs a message voice, for example, "Adjustment of sensor tip is complete" from speaker 504, thereby informing the user that contact adjustment is complete.

At step S106, controller 52 outputs a message voice, for example, "Successively, start measurement" from speaker 504, thereby informing the user that the measurement of a blood sugar level is to be started.

At step S107, controller 52 starts measuring a blood sugar level.

At step S108, controller 52 determines whether the measurement of the blood sugar level is complete. If the measurement is complete, the process proceeds to step S109.

At step S109, controller 52 outputs a message voice, for example, "Measurement is complete" from speaker 504.

At step S110, controller 52 calculates a blood sugar level based on the measured intensity of the infrared light.

At step S111, controller 52 displays the calculated blood sugar level on display 501.

As described above, the present embodiment can measure the contact state between the ATR prism and the measurement skin with high accuracy using the strain sensors attached to the ATR prism.

Embodiment 2

Figure 7:
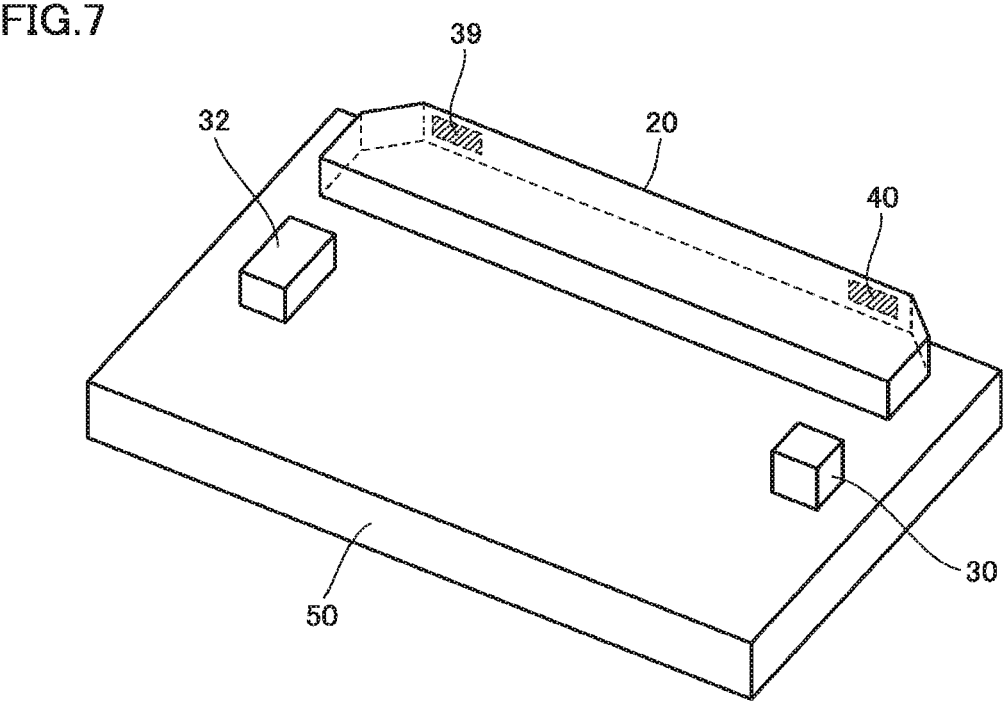
FIG. 7 shows the structure of a sensor head of a non-invasive blood sugar level sensor of Embodiment 2.

FIG. 7 shows the structure of a sensor head of a non-invasive blood sugar level sensor of Embodiment 2. This sensor head includes substrate 50, ATR prism 20, infrared light source 32, infrared photodetector 30, and a surface acoustic wave device, which is a contact sensor of one type. The surface acoustic wave device includes a surface acoustic wave generation unit 39 and a surface acoustic wave detection unit 40.

Substrate 50, ATR prism 20, infrared light source 32, and infrared photodetector 30 are similar to those of Embodiment 1, description of which will not be repeated.

ATR prism 20 has a shape and a material similar to those of Embodiment 1 and is applied with a similar coating. A crystal which has no center-symmetry, such as ZnS or ZnSe of ATR prism 20, exhibits piezoelectric characteristics and has a property of straining upon application of voltage.

Figure 8:
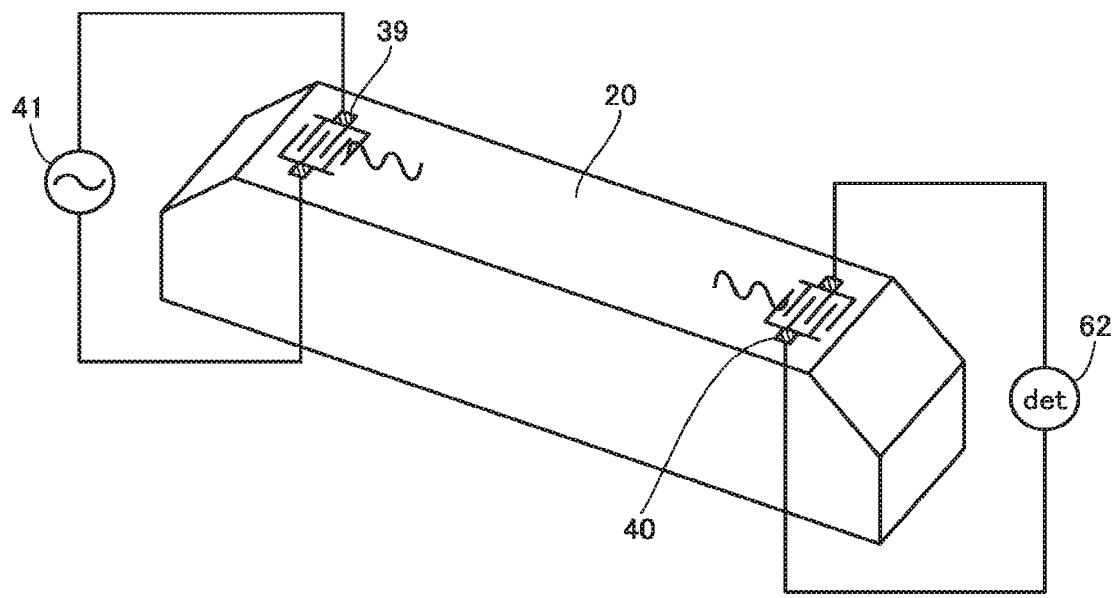
FIG. 8 is a diagram for illustrating a method of measuring a contact state between ATR prism 20 and measurement skin 49 using a surface acoustic wave generation unit 39 and a surface acoustic wave detection unit 40.

FIG. 8 is a diagram for illustrating a method of measuring the contact state between ATR prism 20 and measurement skin 49 using surface acoustic wave generation unit 39 and surface acoustic wave detection unit 40.

As shown in FIG. 8, surface acoustic wave generation unit 39 is formed of a first comb electrode formed at one end of the measuring surface of a plurality of surfaces of ATR prism 20, which is in contact with measurement skin 49. The first comb electrode is connected to an AC voltage power supply 41. Upon application of AC voltage from AC voltage power supply 41, the first comb electrode generates surface acoustic waves.

Surface acoustic wave detection unit 40 is formed of a second comb electrode formed at the other end of the measuring surface of the plurality of surfaces of ATR prism 20, which is in contact with measurement skin 49. The second comb electrode is connected to a detection circuit 62.

The contact stress between ATR prism 20 and measurement skin 49 changes an amplitude or a propagation speed of a surface acoustic wave that is output from surface acoustic wave generation unit 39 and propagates through the measuring surface of ATR prism 20.

Surface acoustic wave detection unit 40 detects a surface acoustic wave that has propagated through the surface of ATR prism 20 and outputs an AC voltage corresponding to the amplitude and phase of the surface acoustic wave. Detection circuit 62 detects the amplitude and phase of the AC voltage output from surface acoustic wave detection unit 40. Controller 52 determines the amplitude and propagation speed of a surface acoustic wave traveling through the measuring surface of ATR prism 20 based on the amplitude and phase of the AC voltage output from surface acoustic wave detection unit 40. Controller 52 determines the contact stress between ATR prism 20 and measurement skin 49 based on the amplitude and propagation speed of the surface acoustic wave.

Figure 9:
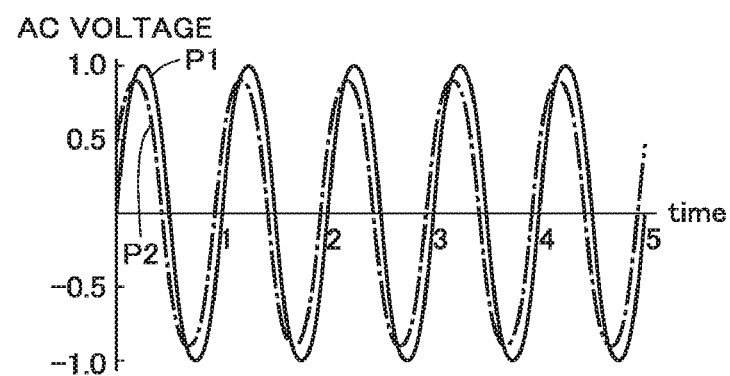
FIG. 9 schematically shows an AC voltage detected by a detection circuit 62 at contact pressures P1 and P2.

FIG. 9 schematically shows AC voltages detected by detection circuit 62 at contact pressures P1 and P2.

With reference to FIG. 9, P1<P2. The amplitude of the AC voltage at a higher contact pressure P2 is smaller than the amplitude of the AC voltage at a lower contact pressure P1. Also, the phase of the AC voltage at higher contact pressure P2 advances more than the phase of the AC voltage at lower contact pressure P1. Thus, a higher contact pressure leads to a smaller amplitude of the surface acoustic wave propagating through the surface of ATR prism 20, which results in a higher propagation speed.

As described above, the present embodiment can measure the contact state between the ATR prism and the measurement skin with high accuracy using the surface acoustic wave device attached to the ATR prism.

Embodiment 3

Figure 10:
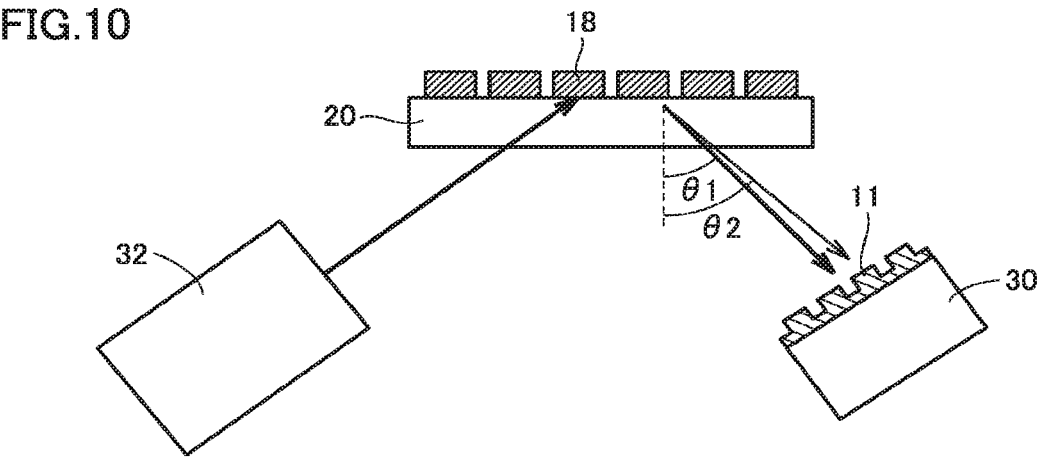
FIG. 10 schematically shows a non-invasive blood sugar level sensor of Embodiment 3.

FIG. 10 schematically shows a non-invasive blood sugar level sensor of Embodiment 3.

The light emitted from infrared light source 32 reaches ATR prism 20, and the incoming light that has passed through ATR prism 20 reaches infrared photodetector 30.

Infrared light source 32 outputs light with a wavelength $\lambda 1$ which is absorbed by sugar of a human body and infrared light with a wavelength $\lambda 2$ for reference which is not absorbed by sugar of a human body. Herein, the effects of infrared rays radiated from a background and a human body are made to be substantially identical to each other by setting wavelengths $\lambda 1$ and $\lambda 2$ to values very close to each other, thus minimizing an effect of noise.

A diffraction grating 18 is provided on the surface of ATR prism 20 which is in contact with measurement skin 49. Diffraction grating 18 may be a diffraction grating having one-dimensional periodic pattern (hereinafter, one-dimensional diffraction grating) or a diffraction grating having a two-dimensional periodic irregular pattern (hereinafter, two-dimensional diffraction grating).

Figure 11:
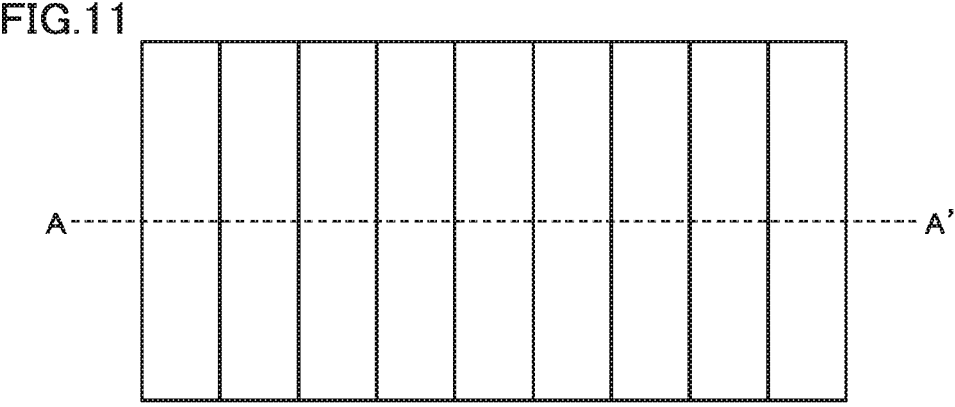
FIG. 11 shows an ATR prism 20 having a one-dimensional diffraction grating as seen from a contact surface between measurement skin 49 and ATR prism 20.
Figure 12:
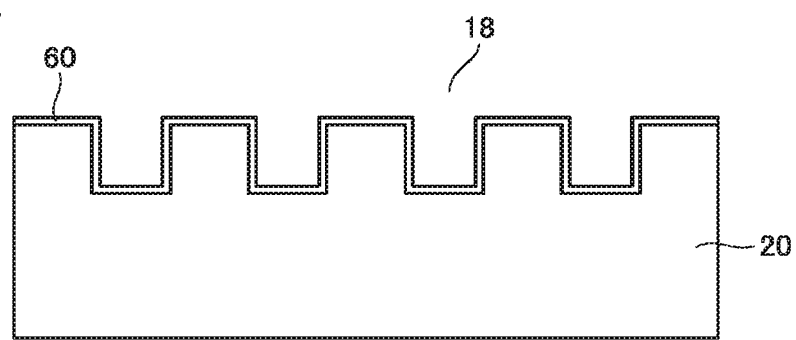
FIG. 12 is a sectional view of ATR prism 20 of FIG. 11, which is taken along A-A' of FIG. 11.

FIGS. 11 and 12 show a diffraction grating having a one-dimensional diffraction grating. FIG. 11 shows ATR prism 20 having a one-dimensional diffraction grating as seen from a contact surface between measurement skin 49 and ATR prism 20. FIG. 12 is a sectional view of ATR prism 20 of FIG. 11, which is taken along A-A' of FIG. 11.

Figure 13:
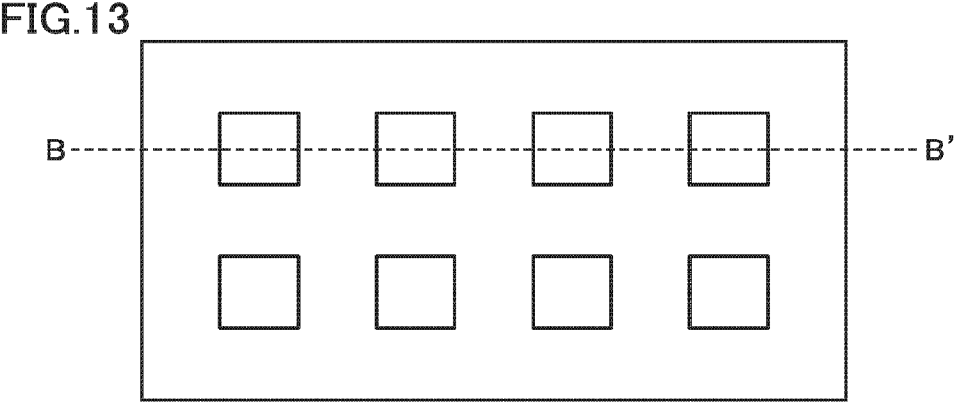
FIG. 13 shows a two-dimensional diffraction grating ATR prism 20 as seen from a contact surface between measurement skin 49 and ATR prism 20.
Figure 14:
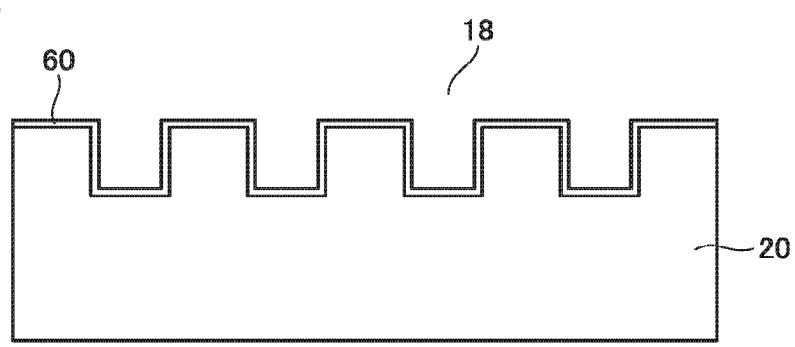
FIG. 14 is a sectional view of ATR prism 20 of FIG. 13, which is taken along B-B' of FIG. 13.

FIGS. 13 and 14 show a diffraction grating having a two-dimensional diffraction grating. FIG. 13 shows a two-dimensional diffraction grating ATR prism 20 as seen from a contact surface between measurement skin 49 and ATR prism 20. FIG. 14 is a sectional view of ATR prism 20 of FIG. 13, which is taken along B-B' of FIG. 13.

For the one-dimensional diffraction grating, whether a diffraction phenomenon occurs, that is, whether a resonance occurs greatly depends on polarization. The interaction between the diffraction grating and the light (incoming light) emitted from infrared light source 32 changes depending on the direction of grooves of the one-dimensional diffraction grating and the direction (polarization) of an electric field. For example, a diffraction phenomenon occurs more easily when the direction of grooves and the direction of an electric field are orthogonal to each other. In contrast, the two-dimensional diffraction grating has a pattern in XY directions, and accordingly, the diffraction phenomenon of the two-dimensional diffraction grating somewhat depends on polarization, though it cannot be said that the diffraction phenomenon greatly depends on polarization compared with the one-dimensional diffraction grating having a pattern only in the one-dimensional X direction. Imparting polarization to incoming light in advance thus causes a diffraction phenomenon more easily.

An angle of reflection θ1 of light with wavelength λ1 and an angle of reflection θ2 of light with wavelength λ2 depend on the pattern of diffraction grating 18, wavelengths λ1 and λ2 of the light radiated from infrared light source 32, polarization of the light with wavelength and the polarization of the light with wavelength λ2. Infrared photodetector 30 is thus positioned so as to perpendicularly receive light emitted from ATR prism 20 at angles of reflection θ1 and θ2.

Diffraction grating 18 is provided on the surface of ATR prism 20 which is in contact with measurement skin 49, thus diffracting the incident light by diffraction grating 18 on the surface. A thin metal film 60 made of, for example, gold is provided on the surface of diffraction grating 18. This causes a surface plasmon resonance of diffraction grating 18. Once the thickness and the metal type of thin metal film 60 are determined, an angle of incidence of the light that enters diffraction grating 18 where a surface plasmon resonance occurs is determined by a wavelength. Consequently, a surface plasmon occurs at an angle of incidence determined by a specific wavelength, thus sensitively determining a wavelength and an angle of incidence by an object (i.e., thin metal film 60) being in contact with diffraction grating 18. Pre-designing this characteristic allows a biological material in an object (measurement skin 49) to be measured with high accuracy by incoming infrared light.

The magnitude of a surface plasmon varies depending on the period and depth of diffraction grating 18 or the size of irregularities. The surface plasmon can be maximized by adjusting the period and depth of diffraction grating 18 to allow signal light (wavelength λ1, λ2) to propagate through the surface or cause the Wood's anomaly. When the surface plasmon reaches its maximum, that is, when an electromagnetic field reaches its maximum, the evanescent light is absorbed most by blood sugar at wavelengths λ1 and λ2, so that the sensitivity of detecting a blood sugar can be increased.

Further, fine control is enabled depending on an angle of incidence and a wavelength. The wavelength of a surface plasmon resonance and the angle of incidence at which a resonance occurs can also be controlled by the periodic structure of diffraction grating 18.

Figure 15:
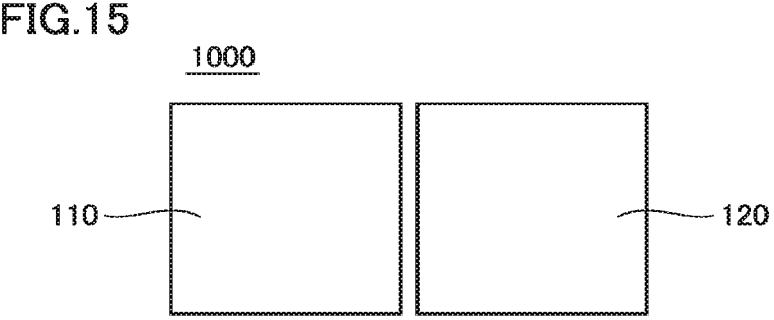
FIG. 15 is a schematic view of a sensor array 1000 of an infrared photodetector 30 of Embodiment 3.

Radiated infrared light 11c radiated from ATR prism 20 is received by infrared photodetector 30. FIG. 15 is a schematic view of a sensor array 1000 included in an infrared photodetector 30 of Embodiment 3. Sensor array 1000 is formed of non-cooling infrared sensors (hereinafter also referred to as sensor pixels) 110 and 120 each detecting light with a different wavelength.

Sensor pixels 110 and 120 each include, for example, a wavelength selection structure 11 using a plasmon resonance on the surface of the light receiving portion. The period of the two-dimensional periodic structure of wavelength selection structure 11 is made almost equal to wavelength λ1 or λ2. Such structure detects the infrared light with the selected wavelength λ1 or λ2. A plurality of wavelengths can be measured simultaneously with the use of infrared photodetector 30 including an array of non-cooling infrared sensors that detect only the infrared light with the selected wavelength λ1 or λ2, enabling measurements in a short period of time. Infrared photodetector 30 having wavelength selectivity can intercept the noise other than signal light (wavelength λ1, λ2), for example, the light radiated from a human body or the surroundings.

Sensor pixels 110 and 120 of infrared photodetector 30 detect infrared light with wavelength λ1 and infrared light with wavelength λ2. The infrared light with wavelength λ1 is absorbed not only by sugar but also by water and any other biological material, whereas the infrared light with wavelength λ2 is not absorbed by sugar but is absorbed by water and any other biological material. Controller 52 thus corrects the intensity of the detected infrared light with wavelength λ1 using the intensity of the infrared light with wavelength λ2 to determine an amount absorbed by sugar. This can improve measurement accuracy.

A degree of adhesion (i.e., the magnitude of a contact stress) between ATR prism 20 and measurement skin 49 changes the refractive index of infrared light at diffraction grating 18. The change in refractive index changes the angle of reflection of light from diffraction grating 18. Thus, an angle of emission of the infrared light is determined uniquely by a degree of adhesion. The use of infrared photodetector 30 can thus determine a degree of adhesion.

A refractive index corresponding to the degree of adhesion (contact stress) between measurement skin 49 and ATR prism 20, an angle of reflection of light from diffraction grating 18 which corresponds to the refractive index, that is, an angle of emission of infrared light from ATR prism 20 are determined in advance.

In measurement of a biological material, infrared photodetector 30 is rotated about a point of emission of infrared light of ATR prism 20. Controller 52 determines an angle of emission of infrared light from ATR prism 20 when infrared photodetector 30 detects the infrared light. Controller 52 determines the degree of adhesion (contact stress) between measurement skin 49 and ATR prism 20, which corresponds to the determined angle of emission. In the present embodiment, the contact stress determined herein is used at step S104 of FIG. 6.

As described above, the present embodiment uses diffraction grating 18 and the sensitive wavelength and incidence angle dependence characteristics of infrared photodetector 30 to determine whether ATR prism 20 and measurement skin 49 adhere to each other with high accuracy, leading to improved accuracy in measuring a blood sugar level.

In order to eliminate external effects, the infrared light detected by infrared photodetector 30 may be chopped by a chopper. At this time, infrared light source 32 per se may be pulse-driven at a constant frequency, and then, the infrared light may be chopped at the frequency to increase detection sensitivity.

Embodiment 4

Measurement skin 49 comes in diffraction grating 18 by pressing ATR prism 20 against measurement skin 49, thus changing a refractive index from that before pressing.

A state, in which measurement skin 49 comes in the entire groove portion of diffraction grating 18 to cause diffraction grating 18 and measurement skin 49 to enter the highest adhesion state without any gap, is referred to as an optimum contact state. In the optimum contact state, evanescent light is absorbed most by sugar, leading to the minimum intensity of reflected light.

Figure 16:
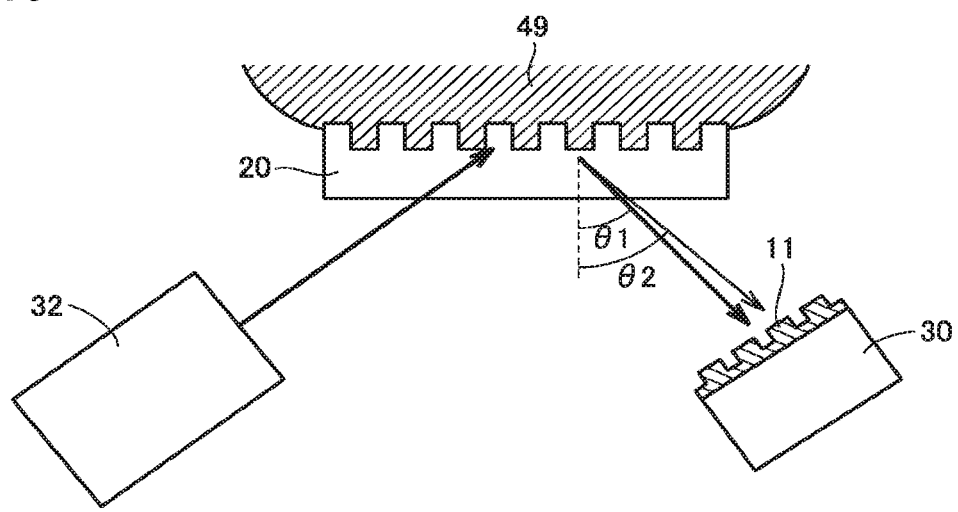
FIG. 16 shows ATR prism 20 and measurement skin 49 in an optimum contact state.

FIG. 16 shows ATR prism 20 and measurement skin 49 in the optimum contact state.

The refractive index of infrared light in the optimum contact state is determined in advance by calculation, and based on the refractive index in the optimum contact state, the angle of reflection of light from diffraction grating 18 is determined in advance. Infrared photodetector 30 is disposed in the direction of this angle of reflection, allowing infrared photodetector 30 to receive the light emitted from ATR prism 20 perpendicularly only in the optimum contact state. Although infrared light enters infrared photodetector 30 in any state other than the optimum contact state, the angle of incidence of the infrared light is not perpendicular as described below, and accordingly, an output from infrared photodetector 30 cannot be obtained.

As described above, the present embodiment can measure an amount of a biological material only when an ATR prism and a measurement skin are in the optimum contact state.

Embodiment 5

Figure 17:
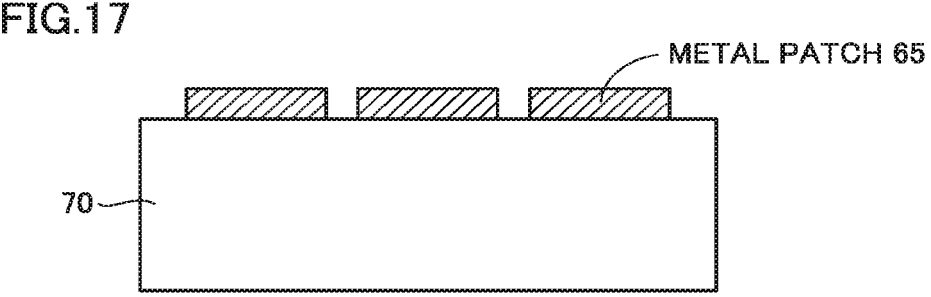
FIG. 17 shows an ATR prism 20 of Embodiment 5.
Figure 18:
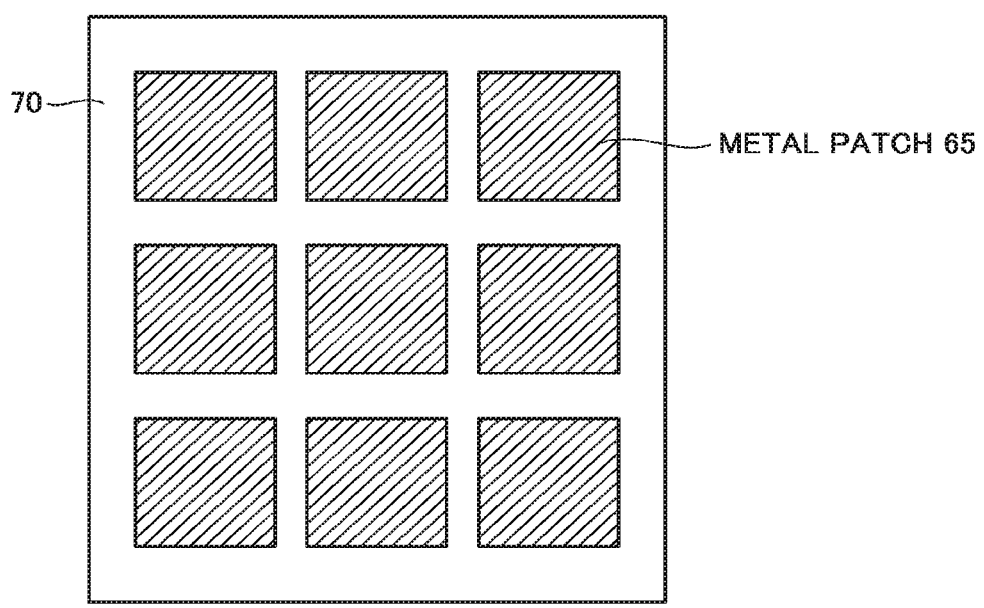
FIG. 18 is a top view of ATR prism 20 of FIG. 17.

FIG. 17 shows an ATR prism 20 of Embodiment 5. FIG. 18 is a top view of ATR prism 20 of FIG. 17.

In Embodiment 5, not a diffraction grating but metal patches 65 are disposed periodically on the contact surface of ATR prism 20 which comes into contact with measurement skin 49. Metal patch 65 preferably has a square, circular, or cross shape. Also, metal patches 65 are preferably disposed two-dimensionally periodically into a tetragonal lattice or triangular lattice. For metal patch 65 having a rectangular shape or an elliptical shape, an asymmetrical shape is provided in a two-dimensional plane, leading to polarization dependence.

Metal patch 65 is a thin film of 50 to 100 nm. If this thickness is sufficiently smaller than a target wavelength, for example, is about a hundredth thereof, no diffraction occurs. In this case, a plasmon resonance depends on the size and period of metal patch 65 and does not depend on the angle of incidence of infrared light on ATR prism 20. Also, the surroundings greatly affect a plasmon resonance wavelength. That is to say, a resonance wavelength is determined by a degree of adhesion between measurement skin 49 and ATR prism 20. For example, for a 2-μm square metal patch 65, if the surrounding is air (i.e., if there is a gap between measurement skin 49 and ATR prism 20), arranging metal patches 65 two-dimensionally periodically in periods of 3 μm results in a resonance wavelength of about 10 μm. A change in the degree of adhesion between measurement skin 49 and ATR prism 20 also changes this value.

Thus, the size and period of metal patch 65 are adjusted such that, when ATR prism 20 and measurement skin 49 enter the highest adhesion state, a plasmon resonance occurs at a wavelength $\lambda$ of infrared light output from infrared light source 32. When the intensity of the detected infrared light reaches its maximum, infrared photodetector 30 can determine that ATR prism 20 and measurement skin 49 are in the highest adhesion state.

In the present embodiment, a resonance wavelength does not depend on the angle of incidence of infrared light on ATR prism 20, and accordingly, the accuracy of an angle, at which ATR prism 20 is installed with respect to infrared light source 32, is of no concern. This yields an effect of accuracy improvement; for example, a mobile device has high resistance to vibrations.

As described above, the present embodiment can measure an amount of a biological material only when an ATR prism and a measurement skin are in the optimum contact state.

Embodiment 6

Figure 19:
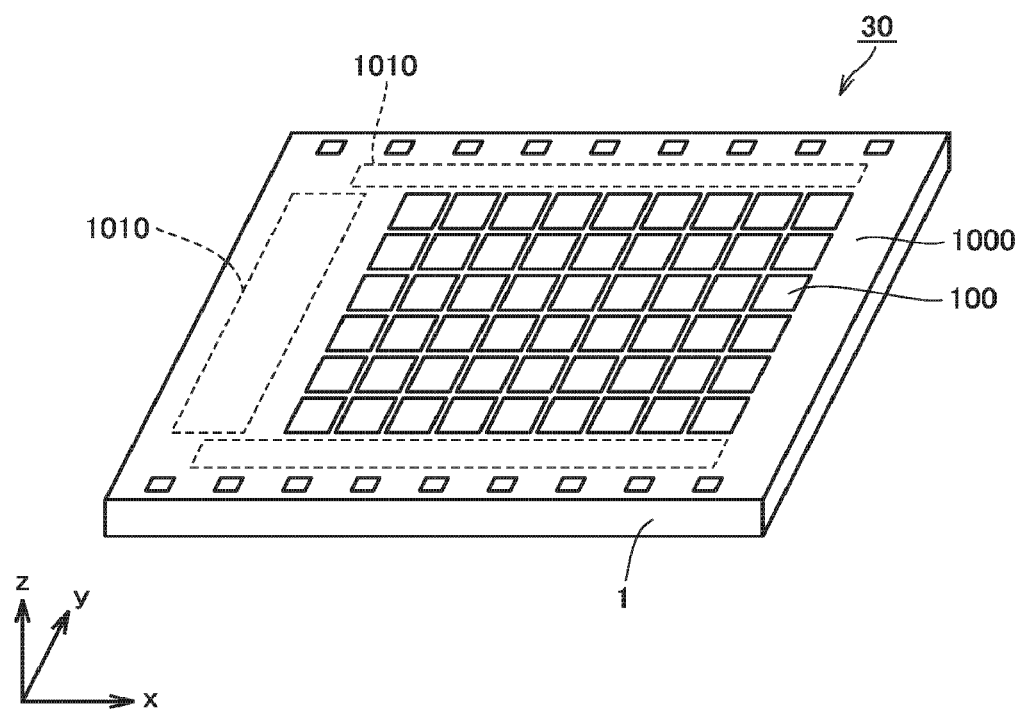
FIG. 19 shows a configuration of an infrared photodetector 30 of Embodiment 6.

FIG. 19 shows a configuration of an infrared photodetector 30 of Embodiment 6.

Infrared photodetector 30 is an integrated wavelength-selective infrared sensor. Infrared photodetector 30 includes a sensor array 1000 and a detection circuit 1010.

Sensor array 1000 includes 9×6 pixels (semiconductor optical devices) 100 arranged in rows and columns. On substrate 1, 9×6 semiconductor optical devices 100 are arranged in matrix (in array) in the X-axis and Y-axis directions. Light enters from the direction parallel to the Z-axis.

Detection circuit 1010 is provided around sensor array 1000. Detection circuit 1010 processes a signal detected by semiconductor optical device 100 to detect an image. When the detected wavelengths are fewer, detection circuit 1010 is not required to detect an image and is merely required to detect an output from each device.

Description will now be given by taking a thermal infrared sensor as an example of semiconductor optical device 100.

Figure 20:
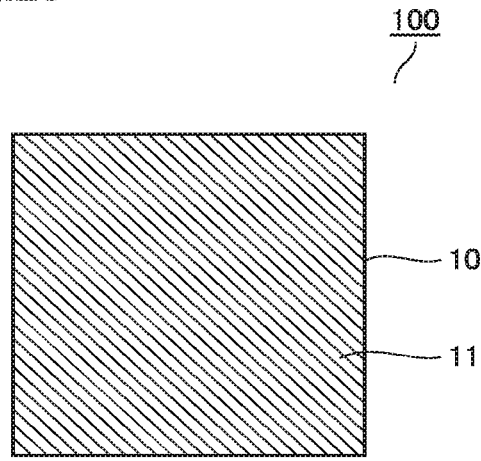
FIG. 20 is a top view of a semiconductor optical device 100 of Embodiment 6.

FIG. 20 is a top view of semiconductor optical device 100. Semiconductor optical device 100 includes an absorber 10.

Figure 21:
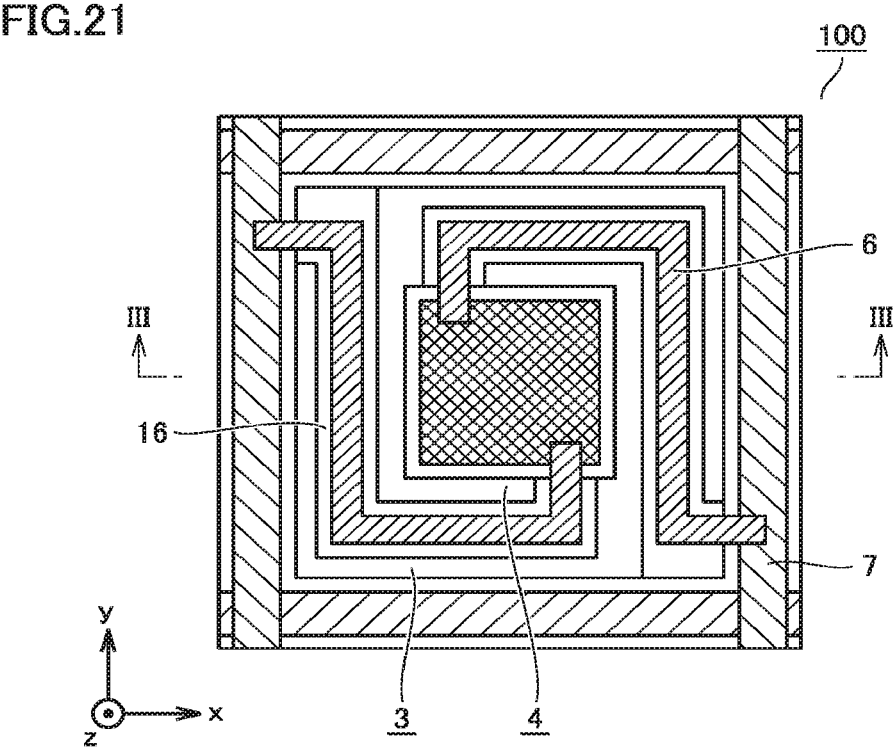
FIG. 21 is a top view of semiconductor optical device 100, where absorber 10 is omitted.
Figure 22:
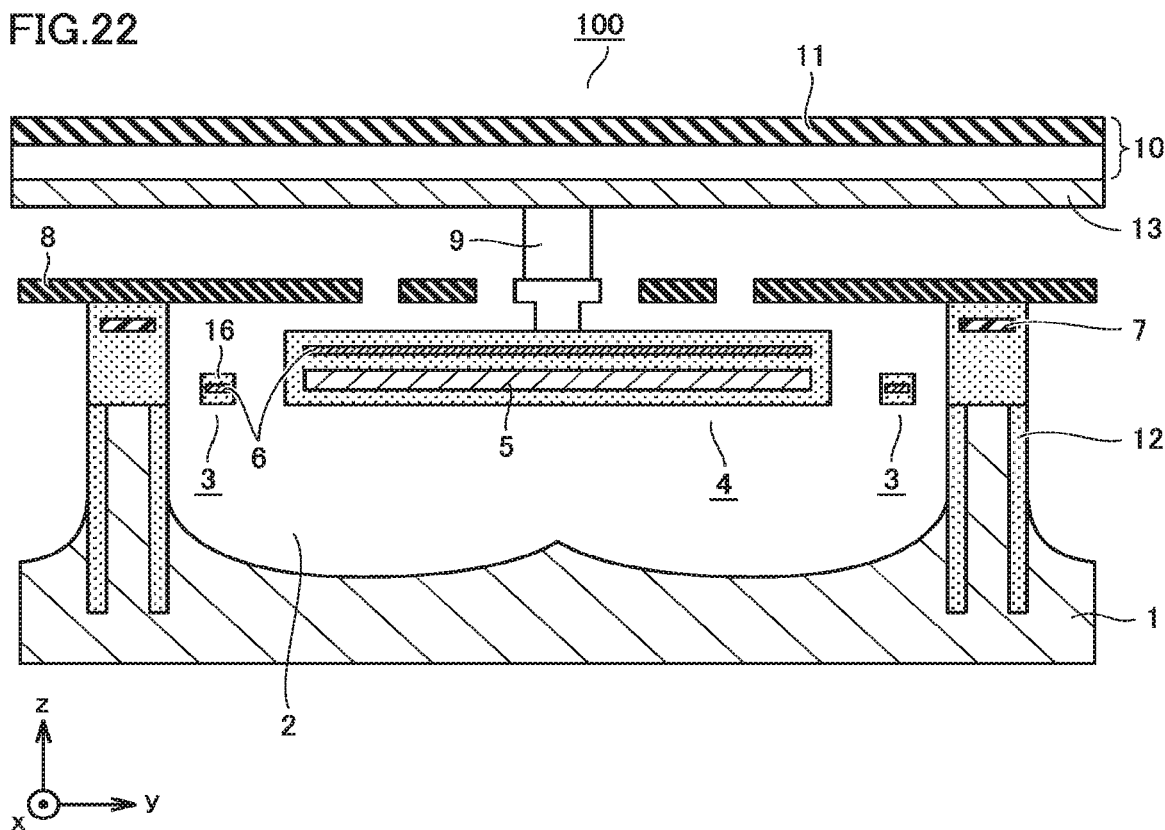
FIG. 22 is a sectional view (including absorber 10 and the like) when semiconductor optical device 100 of FIG. 21 is viewed in a direction.
Figure 23:
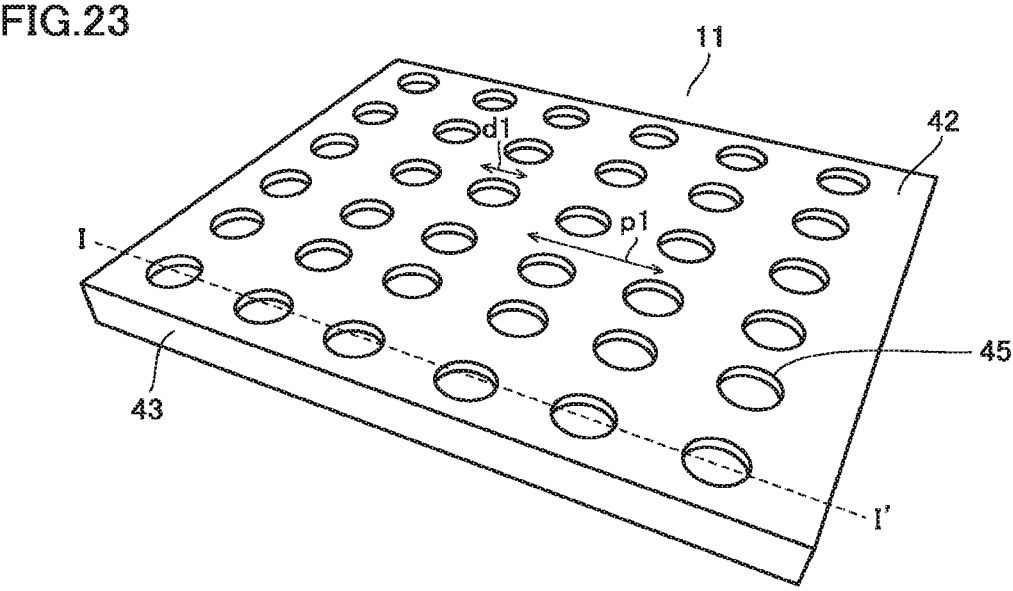
FIG. 23 shows an absorber 10 of semiconductor optical device 100.

FIG. 21 is a top view of semiconductor optical device 100, where absorber 10 is omitted. FIG. 21 does not show a protective film or a reflection film on a wire for clarification. FIG. 22 is a sectional view (including absorber 10 and the like) of semiconductor optical device 100 of FIG. 21, as seen in the III-III direction of FIG. 21. FIG. 23 shows absorber 10 of semiconductor optical device 100.

As shown in FIGS. 19 to 22, semiconductor optical device 100 includes, for example, a substrate 1 made of silicon. A hollow 2 is provided in substrate 1. A temperature detection unit 4 that detects temperatures is disposed above hollow 2. Temperature detection unit 4 is supported by two support legs 3. As shown in FIG. 21, support leg 3 has a bridge shape bent in an L-shape as seen from above. Support leg 3 includes a thin metal wire 6 and a dielectric film 16 supporting thin metal wire 6.

Temperature detection unit 4 includes a detection film 5 and thin metal wire 6. Detection film 5 is formed of, for example, a diode containing crystal silicon. Thin metal wire 6 is also provided in support leg 3 and electrically connects an aluminum wire 7 and detection film 5, which are covered with an insulating film 12, to each other. Thin metal wire 6 is made of, for example, titanium alloy having a thickness of 100 nm. An electric signal output from detection film 5 is transmitted to aluminum wire 7 through thin metal wire 6 formed in support leg 3 and is extracted by detection circuit 1010 of FIG. 19. An electric connection between thin metal wire 6 and detection film 5 and between thin metal wire 6 and aluminum wire 7 may be provided via a conductor (not shown) extending thereabove or therebelow if necessary.

Reflective film 8 that reflects infrared rays is disposed to cover hollow 2; however, it is disposed to cover at least part of support leg 3 with reflective film 8 and temperature detection unit 4 not being thermally connected to each other.

As shown in FIG. 22, a support pillar 9 is provided above temperature detection unit 4. Absorber 10 is supported on support pillar 9. That is to say, absorber 10 is connected to temperature detection unit 4 by support pillar 9. Since absorber 10 is thermally connected to temperature detection unit 4, a change in the temperature generated in absorber 10 is conveyed to temperature detection unit 4.

At the same time, absorber 10 is disposed above reflective film 8 while it is not thermally connected to reflective film 8. Absorber 10 extends laterally in a plate shape so as to cover at least part of reflective film 8. As seen from above, thus, only absorber 10 is viewed in semiconductor optical device 100 as shown in FIG. 20. Alternatively, absorber 10 may be formed directly on temperature detection unit 4.

In the present embodiment, wavelength selection structure 11 that selectively absorbs light with a certain wavelength is provided in the surface of absorber 10, as shown in FIG. 22. Also, an anti-absorption film 13 that prevents light absorption from the rear surface is provided on the rear surface of absorber 10, that is, on the support pillar 9 side. This configuration allows absorber 10 to selectively absorb light with a certain wavelength. Since wavelength selection structure 11 may absorb light, absorber 10 in the present embodiment includes wavelength selection structure 11.

Description will now be given of a case in which wavelength selection structure 11 is configured to use a surface plasmon. Providing a periodic structure made of metal in a light incidence surface causes a surface plasmon at a wavelength corresponding to a surface periodic structure, so that light is absorbed. Thus, the surface of absorber 10 can be made of metal to control the wavelength selectivity of absorber 10 by a wavelength of incident light, an angle of incidence, and a periodic structure of the metal surface.

In the present embodiment, a phenomenon in which free electrons inside a metal film make contribution and the generation of a surface mode by a periodic structure are regarded as being synonymous with each other in terms of absorption, and they are merely referred to as a surface plasmon or a surface plasmon resonance, or merely as a resonance without differentiating therebetween. Although they may also be referred to as a pseudo-surface plasmon and a metamaterial, they are treated similarly as a phenomenon in terms of absorption. The configuration of the present embodiment is also effective for light with a wavelength in a wavelength region other than infrared light, for example, a visible region, a near infrared region, and a THz region.

As shown in FIG. 23, wavelength selection structure 11 that selectively increases the absorption of light having a certain wavelength, which is provided in the surface of absorber 10, includes a metal film 42, a main body 43, and recesses 45.

The type of metal film 42 provided on the surface of absorber 10 is selected from metals that easily cause a surface plasmon resonance, such as Au, Ag, Cu, Al, Ni, and Mo. Alternatively, the type of metal film 42 may be a material that easily causes a plasmon resonance, such as metallic nitrides including TiN, metallic borides, and metallic carbides. It suffices that metal film 42 in the surface of absorber 10 has such a thickness as not to allow incoming infrared light to pass therethrough. With such a film thickness, only a surface plasmon resonance in the surface of absorber 10 affects absorption and radiation of electromagnetic waves, and the material below metal film 42 does not optically affect absorption or the like.

A thickness (skin depth) $\delta 1$ of a skin effect is represented by expression below:

$$\delta 1 = (2/\mu\sigma\omega)^{1/2}$$

where $\mu$ is a magnetic permeability of metal film 42, $\sigma$ is an electric conductivity of metal film 42, and $\omega$ is an angular frequency of incident light.

For example, when film thickness $\delta$ of metal film 42 in the surface of absorber 10 is at least twice $\delta 1$, that is, from about several tens of nanometers to about several hundreds of nanometers, a leak of incident light to below absorber 10 can be made sufficiently small.

For example, in comparison of heat capacity between gold and oxide silicon ($SiO_2$), oxide silicon has a smaller heat capacity. An absorber formed of main body 43 made of oxide silicon and the surface of metal film 42 made of gold can have a smaller heat capacity than an absorber made of gold alone, and accordingly, can have a higher response.

A method of manufacturing absorber 10 will now be described.

A periodic structure is formed on the front surface side of main body 43 formed of a dielectric or semiconductor by photolithography and dry etching, and then, metal film 42 is formed by sputtering or the like. Similarly for the rear surface, subsequently, a periodic structure is produced, and then, metal film 42 is formed.

Since the diameter of recess 45 is as small as about several micrometers, a manufacturing step is more simplified by forming metal film 42 after etching main body 43 to form recesses than by directly etching metal film 42 to form recesses. Since an expensive material such as Au or Ag is used for metal film 42, the use of main body 43 of dielectric or semiconductor can reduce the amount of metal used for reduced cost.

The characteristics of absorber 10 will now be described with reference to FIG. 23. Cylindrical recesses 45 each having a diameter d of 4 μm and a depth h of 1.5 μm are arranged in tetragonal lattice in periods p of 8 μm. In this case, an absorption wavelength is about 8 μm. Alternatively, cylindrical recesses 45 each having a diameter d of 4 μm and a depth h of 1.5 μm are arranged in tetragonal lattice in periods p of 8.5 μm. In this case, an absorption wavelength is almost about 8.5 μm.

A relationship between the absorption wavelength and radiation wavelength of incident light and the period of recess 45 is almost identical to each other in, for example, a tetragonal lattice arrangement and a triangular lattice arrangement as long as they have a two-dimensional periodic structure, and an absorption wavelength and a radiation wavelength are determined by the period of recess 45. Considering reciprocal vectors of the periodic structure, theoretically, the absorption and radiation wavelengths are almost identical to the period in the tetragonal lattice arrangement, whereas the absorption and radiation wavelengths are equal to a period×√3/2 in the triangular lattice arrangement. In actuality, however, the absorption and radiation wavelengths vary slightly depending on diameter d of recess 45. It is thus conceivable that incident light may be absorbed or radiated at a wavelength almost identical to a period in both the periodic structures.

The wavelength of infrared light to be absorbed can thus be controlled by the period of recess 45. Generally, diameter d of recess 45 is desirably not less than a half of period p. If diameter d of recess 45 is smaller than a half of period p, a resonance effect tends to be smaller to reduce an absorptivity. However, since a resonance is a three-dimensional resonance in recess 45, a sufficient absorption may be achieved even when diameter d is smaller than a half of period p. The value of diameter d with respect to period p is accordingly designed individually as appropriate. What is important is that an absorption wavelength is controlled mainly by period p. When diameter d is not less than a certain value with respect to period p, absorber 10 has sufficient absorption characteristics, providing ranges to design. Meanwhile, referring to a general expression of dispersion relation of a surface plasmon, the light to be absorbed is irrelevant to depth h of recess 45 and depends on period p alone. The absorption wavelength and radiation wavelength thus do not depend on depth h of recess 45 shown in FIG. 23.

Although the absorber having recesses 45 arranged periodically has been described above, similar effects can be achieved also with the structure having projections arranged periodically.

The absorption by absorber 10 having such an irregular structure is greatest in the case of normal incidence. When the angle of incidence on absorber 10 deviates from that of normal incidence, the absorption wavelength also changes, leading to a smaller absorption.

As described above, the use of the infrared photodetector described in the present embodiment can also achieve the effects similar to those described in Embodiments 1 to 5.

MODIFICATIONS

The present invention is not limited to the above embodiments and includes, for example, a modification below.

(1) Contact Sensor

The contact sensor that detects a pressure caused by contact between ATR prism 20 and measurement skin 49 may also be a capacitive sensor, a semiconductor piezoresistance sensor, a silicon resonant sensor, or any other sensor other than in Embodiment 1 and Embodiment 2.

It is to be understood that the embodiments disclosed herein are presented for the purpose of illustration and non-restrictive in every respect. It is therefore intended that the scope of the present invention is defined by claims, not only by the embodiments described above, and encompasses all modifications and variations equivalent in meaning and scope to the claims.

REFERENCE SIGNS LIST 1, 50 substrate, 2 hollow, 3 support leg, 4 temperature detection unit, 5 detection film, 6 thin metal wire, 7 aluminum wire, 8 reflective film, 9 support pillar, 10 absorber, 11 wavelength selection structure, 11a incoming infrared light, 11b propagating infrared light, 11c radiated infrared light, 12 insulating film, 13 anti-absorption film, 14 metal layer, 16 dielectric film, 18 diffraction grating, 20 ATR prism, 20a, 20b, 20c, 20d ATR prism end face, 30 infrared photodetector, 32 infrared light source, 36 support, 37a, 37b, 37c strain, 38a, 38b, 38c measurement circuit, 39 surface acoustic wave generation unit, 40 surface acoustic wave detection unit, 41 AC voltage power supply, 42 metal film, 43 main body, 45 recess, 49 measurement skin, 52 controller, 54 user interface, 60 thin metal film, 62 detection circuit, 65 metal patch, 100 semiconductor optical device, 110, 120 non-cooling infrared sensor, 501 display, 502 vibrator, 503 keyboard, 504 speaker, 1000 sensor array, 1010 detection circuit.

The invention claimed is:

1. A biological material measuring apparatus comprising:
    an infrared light source configured to radiate infrared light in entirety or part of a wavelength region with absorption wavelengths of a biological material;
    an ATR prism having a first end face, a second end face, a third end face, and a fourth end face and configured to receive, on the first end face, infrared light radiated from the infrared light source, cause the received infrared light to pass therethrough while repeating total reflection off the second end face and the third end face, and emit the infrared light that has passed therethrough from the fourth end face;
    an infrared photodetector configured to detect the infrared light emitted from the ATR prism while separating wavelengths; and
    a contact sensor attached to the ATR prism and configured to detect a contact state between the ATR prism and a living body surface, the contact sensor being disposed so as not to be in direct contact with the living body surface, the contact sensor includes a plurality of strain sensors including a first strain sensor disposed on a first surface of the ATR prism and a second strain sensor disposed on a second surface of the ATR prism.

2. The biological material measuring apparatus according to claim 1, wherein each of the plurality of strain sensors is a thin metal layer having a resistance which changes due to expansion and contraction strains which are caused by an applied force.

3. The biological material measuring apparatus according to claim 2, comprising:
    a support supporting the ATR prism; and
    a substrate on which the ATR prism and the support are placed, wherein
    the first surface of the ATR prism and the substrate are in contact with each other, the first surface being perpendicular to a surface of the ATR prism which is configured to be in contact with the living body surface, and
    the second surface of the ATR prism and the support are in contact with each other, the second surface being opposite to the surface of the ATR prism which is configured to be in contact with the living body surface.

4. The biological material measuring apparatus according to claim 1, wherein the contact stale includes information on a contact angle between the ATR prism and the living body surface.

5. The A biological material measuring apparatus comprising:
    an infrared light source configured to radiate infrared light in entirety or part of a wavelength region with absorption wavelengths of a biological material;
    an ATR prism having a first end face, a second end face, a third end face, and a fourth end face and configured to receive, on the first end face, infrared light radiated from the infrared light source, cause the received infrared light to pass therethrough while repeating total reflection off the second end face and the third end face, and emit the infrared light that has passed therethrough from the fourth end face;

an infrared photodetector configured to detect the infrared light emitted from the ATR prism while separating wavelengths; and a contact sensor attached to the ATR prism and configured to detect a contact state between the ATR prism and a living body surface, wherein the contact sensor is a surface acoustic wave device attached to a surface of the ATR prism that is configured to contact the living body surface.

6. The biological material measuring apparatus according to claim 5, wherein the surface acoustic wave device includes a first comb electrode formed at one end of a surface of the ATR prism which is in contact with the living body surface, and a second comb electrode formed at another end of the surface of the ATR prism which is in contact with the living body surface, and the biological material measuring apparatus further comprises:

an AC voltage power supply connected to the first comb electrode; and a detection circuit connected to the second comb electrode and configured to detect an amplitude and a phase of an AC voltage output from the second comb electrode.

7. A biological material measuring apparatus comprising:

an infrared light source configured to radiate infrared light in entirety or part of a wavelength range with absorption wavelengths of a biological material; and an ATR prism having a first end face, a second end face, a third end face, and a fourth end face and configured to receive, on the first end face, infrared light radiated from the infrared light source, cause the received infrared light to pass therethrough while repeating total reflection off the second end face and the third end face, and emit the infrared light that has passed therethrough from the fourth end face, and an infrared photodetector configured to detect an intensity of the infrared light emitted from the ATR prism, wherein a surface of the ATR prism has a diffraction grating formed one-dimensionally or two-dimensionally periodically, a surface of the diffraction grating has a thin metal film formed thereon, and a period and a depth of the diffraction grating are adjusted such that, when a contact state between the ATR prism and a living body surface is a highest adhesion state, a plasmon resonance is maximized at a wavelength of the infrared light received from the infrared light source.

8. The biological material measuring apparatus according to claim 7, wherein a surface of a light receiving portion of the infrared photodetector has recesses or protrusions formed periodically therein, and a diffraction grating formed on a surface of the ATR prism reflects infrared light with the wavelength which has been received from the infrared light source and the reflected infrared light perpendicularly enters the surface of the light receiving portion.

9. The biological material measuring apparatus according to claim 8, wherein at least an outermost surface of the light receiving portion is made of a material that generates a surface plasmon resonance.

10. The biological material measuring apparatus according to claim 7, wherein when a contact state between the ATR prism and the living body surface is a highest contact state, the infrared light emitted from the ATR prism perpendicularly enters the infrared photodetector.

11. A biological material measuring apparatus comprising:

an infrared light source configured to radiate infrared light in entirety or part of a wavelength range with absorption wavelengths of a biological material;

an ATR prism having a first end face, a second end face, a third end face, and a fourth end face and configured to receive, on the first end face, infrared light radiated from the infrared light source, cause the received infrared light to pass therethrough while repeating total reflection off the second end face and the third end face, and emit the infrared light that has passed therethrough from the fourth end face;

an infrared photodetector configured to detect an intensity of the infrared light emitted from the ATR prism; and metal patches disposed periodically on a surface of the ATR prism, wherein sizes and periods of the metal patches are adjusted such that, when a contact state between the ATR prism and a living body surface is a highest adhesion state, a plasmon resonance occurs at a wavelength of the infrared light output from the infrared light source.

12. The biological material measuring apparatus according to claim 11, wherein a surface of a light receiving portion of the infrared photodetector has recesses or protrusions formed periodically therein, and a diffraction grating formed on a surface of the ATR prism reflects infrared light with the wavelength which has been received from the infrared light source and the reflected infrared light perpendicularly enters the surface of the light receiving portion.

13. The biological material measuring apparatus according to claim 12, wherein at least an outermost surface of the light receiving portion is made of a material that generates a surface plasmon resonance.

14. The biological material measuring apparatus according to claim 11, wherein when a contact state between the ATR prism and the living body surface is a highest contact state, the infrared light emitted from the ATR prism perpendicularly enters the infrared photodetector.

* * * * *